United States Patent [19]

Koch

[11] Patent Number: 5,284,476
[45] Date of Patent: Feb. 8, 1994

[54] NUCLEAR HYDROLYSIS CANNULA

[76] Inventor: Paul S. Koch, 15 Red Oak Rd., East Greenwich, R.I. 02818

[21] Appl. No.: 854,701

[22] Filed: Mar. 20, 1992

[51] Int. Cl.$^5$ .............................................. A61M 5/32
[52] U.S. Cl. .................................. 604/274; 604/272; 606/166
[58] Field of Search .............................. 604/272–274, 604/22, 239, 264, 51, 283; 606/166

[56] References Cited

U.S. PATENT DOCUMENTS

| | | |
|---|---|---|
| 1,384,355 | 7/1921 | Smith . |
| 2,601,580 | 6/1952 | Yanus . |
| 2,748,769 | 6/1956 | Huber .................. 604/272 |
| 2,850,014 | 9/1958 | Ginsburg . |
| 2,899,959 | 8/1959 | Ginsburg . |
| 3,097,647 | 7/1963 | Roehr . |
| 4,013,080 | 3/1977 | Froning . |
| 4,377,897 | 3/1983 | Eichenbaum et al. . |
| 4,383,530 | 5/1983 | Bruno .................. 604/274 |
| 4,386,927 | 6/1983 | Eichenbaum . |
| 4,496,353 | 1/1985 | Overland et al. . |
| 4,511,356 | 4/1985 | Froning et al. ............ 604/164 |
| 4,518,383 | 5/1985 | Evans . |
| 4,538,611 | 9/1985 | Kelman . |
| 4,577,629 | 3/1986 | Martinez . |
| 4,705,500 | 11/1987 | Reimels et al. . |
| 4,759,746 | 7/1988 | Straus .................. 604/51 |
| 4,808,170 | 2/1989 | Thornton et al. . |
| 4,889,529 | 12/1989 | Haindl ................. 604/274 |
| 4,908,015 | 3/1990 | Anis . |

Primary Examiner—C. Fred Rosenbaum
Assistant Examiner—V. Alexander
Attorney, Agent, or Firm—Mason, Fenwick & Lawrence

[57] ABSTRACT

A cannula for use in cataract surgery during the phases of hydrodissection and hydrodelamination/hydrodelineation/hydrodemarcation is described. The cannula has a hub for mating with a syringe and a needle originating from the distal end of the hub. The needle comprises a first section, second section, and truncated surface. The first section originates from the distal end of the hub and extends forward in a plane delineating the central longitudinal axis of the cannula. The second section originates from the distal end of the first section and is flattened and curved away from the central longitudinal axis of the hub. The truncated surface of the needle forms a rounded tip with beveled surfaces. The intersection of the bevel and sides of the cannula are sharpened to provide a cutting edge.

26 Claims, 2 Drawing Sheets

NUCLEAR HYDROLYSIS CANNULA

FIELD OF THE INVENTION

This invention relates generally to cannulas and relates more particularly to cannulas for use in removing cataracts during the surgical phases of hydrodissection and hydrodelamination/hydrodelineation/hydrodemarcation.

BACKGROUND OF THE INVENTION

Embryologically, the human lens forms with a fetal nucleus which, after development, becomes the center of the crystalline lens. The inner side of the anterior capsule of the lens contain epithelial cells which migrate peripherally and posteriorly to lay down concentric lamellae of nuclear tissue. An adult nucleus next forms around the fetal nucleus and concentrically disposed lamellae, and the lens takes shape.

Throughout life, the epithelial cells continue to migrate and lay down lamellae of nuclear tissue. However, because the lens is now enclosed by the adult nucleus, the area of lens growth is confined causing the layers to become compressed and tightly packed. This increased compression and packing causes the lens to become stiff and firm, and by the age of 40 the ability of the lens to flex and focus is greatly reduced. As successive layers continue to be deposited, the lens becomes so dense that it begins to change color and the clarity is lost. At this point, the successively deposited layers of lamellae are referred to as a cataract. The inner nucleus of the cataract consists of a firm, dense material while the outer nucleus consists of a less dense material. The material surrounding the nucleus of a cataractous lens is known as the cortex.

Different terms are used to describe the surgical steps of separating the nucleus into its various components. Hydrodissection usually refers to an irrigation of fluid between the anterior capsule and the outer nucleus, essentially separating the outer nucleus from the cortex and even separating some cortex from itself.

The terms hydrodelineation, hydrodelamination, and hydrodemarcation are all synonymous and refer to the injection of fluid within the body of the cataract to separate the inner nucleus from the outer nucleus. In some instances, it is possible to cause multiple separations of the inner nucleus into several nuclei. This multiple separation is referred to as multilamellar delineation.

The instruments typically used to perform this function are blunt tipped cannulas generally between 25 and 30 gauge in diameter. The cannulas are attached to a syringe containing a balanced salt solution. During surgery, the rounded tip of the cannula is thrust into the wall of the capsular bag and into the lens therein to obtain a cleavage plane. A salt solution is injected into the cataract and the nucleus of the lens is hydrodelineated and decompacted.

Multilamellar delineation during the surgical phase of hydrodelineation may be accomplished using hydrosonics based on technology licensed to Alcon Corporation by Azis Aniz, M.D. A small needle is attached to an ultrasonic handpiece and high frequency ultrasound activates the tip, permitting deep penetration of the nucleus. A salt solution is injected into the nucleus and several cleavage planes (multilamellar delineation) are obtained due to the vibrating tip coming in contact with several lamellae. Unfortunately, this device costs just under $20,000.

A needle useful in ophthalmic surgery is disclosed by Thorton et al., U.S. Pat. No. 4,808,170. The needle is designed to administer posterior peribulbar or retro-bulbar anesthesia and contains a beveled tip on the distal end of the needle. The object of the needle is to penetrate by separating tissue instead of cutting tissue, therefore the tip and sides of the tip are rounded to provide a smooth transition between the bevel tip and side surfaces of the needle.

Straus, U.S. Pat. No. 4,759,746, discloses a retro-bulbar needle. The needle is for use in administering retrobulbar or peribulbar anesthetics. The curved needle extends outwardly away from the longitudinal axis of the hub and then extends inwardly towards the longitudinal axis concluding with a terminal section which is straight and oriented at a predetermined angle to the longitudinal axis. The tip of the needle is rounded and beveled and the bevel is towards the concave aspect of the curved needle. The needle is curved so as to reduce the risk of retro-bulbar hemorrhage by violating less orbital space.

There are several structures of needles disclosed in other arts similar in construction to the apparatus disclosed herein such that they warrant discussion although they do not anticipate or make obvious the present invention. One such needle is disclosed by Yanus, U.S. Pat. No. 2,601,580. A portion of the needle shank is flattened by rollers to reduce the pain incurred by a patient when an otherwise rounded needle of equivalent cross sectional area is used. Also, the needle is beveled at the distal end and the beveled sides are sharpened to function as cutting edges.

Ginsburg, U.S. Pat. No. 2,899,959, discloses a hypodermic needle. The needle comprises a shank wherein the upper and lower shank sections are substantially parallel to each other and the axis of the intermediate part of the shank forms an obtuse angle with the axis of the upper section and an obtuse angle with the lower section. Also, the tip of the lower shank portion is beveled. The structure disclosed by Ginsburg helps to reduce problems normally associated with straight shanks such as the insertion point frequently scratching the vein walls causing pain, excessive limb movement causing the needle to slip out, and potential that a straight shank will not properly position itself for injection or withdrawal of blood.

Froning, U.S. Pat. No. 4,013,080, discloses a cannula connector useful in lumbar disc puncture. When the cannula is in proximity to the disc to be treated, a disc penetrating needle is inserted into the lumen o the cannula. The needle has a male luer-lock fitting for attachment to a syringe at its proximal end and a beveled tip at the distal end. The terminal section of the needle is also curved. The terminal section of the needle is curved to facilitate the maneuverability of the needle around obstacles.

While the prior art needles disclose structures with rounded beveled tip, curved shanks and flattened portions (in certain combinations), these needles are not suitable for obtaining multilamellar delineation during the cataract surgery phase of hydrodelineation/hydrodelamination/hydrodemarcation. One such method of achieving multilamellar delineation is through the hydrosonics device licensed to Alcon Corporation by Azis Aniz, M.D., however, this device is expensive as was noted previously.

Thus, there is a need for an inexpensive cannula for use in cataract surgery during the surgical phases of hydrodissection and hydrodelamination/hydrodelineation/hydrodemarcation.

Therefore, it is a primary object of this invention to provide an economically disposable cannula for use in cataract surgery during the surgical phases of hydrodissection and hydrodelamination/hydrodelineation/hydrodemarcation.

Another object of this invention is to provide an inexpensive cannula for use in cataract surgery that will isolate several cleavage planes (multilamellar delineation) during the surgical phase of hydrodelamination/hydrodelineation/hydrodemarcation.

A further object of this invention is to provide a curved cannula for use in cataract surgery that will permit better control of the instrument during the surgical phase of hydrodissection.

Another object of this invention is to provide a cannula for use in cataract surgery with a flattened shank section to rotate the nucleus during the surgical phases of hydrodelamination/hydrodelineation/hydrodemarcation and obtain improved cleavage of the nucleus when compared to circular cross-sectional cannulas.

Another object of this invention is to provide a cannula with a short length of needle to enable the cannula hub to be close to the eye thereby reducing unwanted leverage.

Still another object of this invention is to provide a cannula with a rounded tip and sharpened sides to engage, penetrate and irrigate additional tissue.

SUMMARY OF THE INVENTION

These and other objects of the present invention are achieved in the preferred embodiment of the present invention. The present invention comprises a cannula for use in cataract surgery during the surgical phases of hydrodissection and hydrodelamination/hydrodelineation/hydrodemarcation. The cannula is composed of a hub portion with a centrally disposed longitudinal axis therethrough and a needle portion extending from the hub. The distal end of the needle has a rounded tip which is beveled. Also, the needle has a flattened side surface extending from its midsection to its outer beveled rounded tip. Further, the portion of the needle including the flattened surface curves outwardly away from the longitudinal axis of the cannula from the inner end of the flattened portion to its rounded tip.

A better understanding of the manner in which the preferred embodiment achieves the objects of the invention will be obtained when the following detailed description is considered in conjunction with the appended drawings in which like reference numerals are employed in the different figures for identification of the same component parts of the preferred embodiment.

DESCRIPTION OF THE PREFERRED EMBODIMENT

Figure 1:
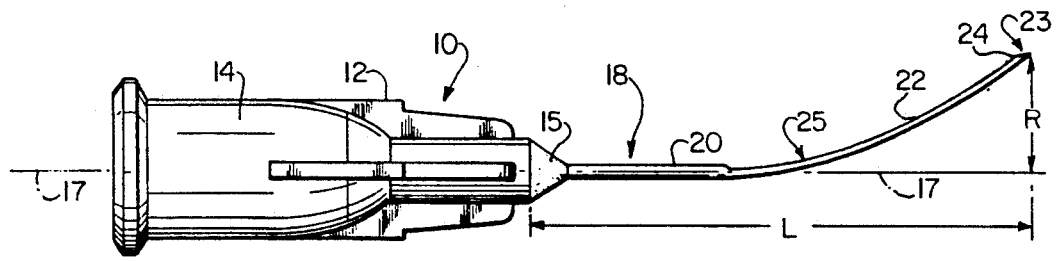
FIG. 1 is a top plan view of the preferred embodiment of the cannula of the present invention.
Figure 2:
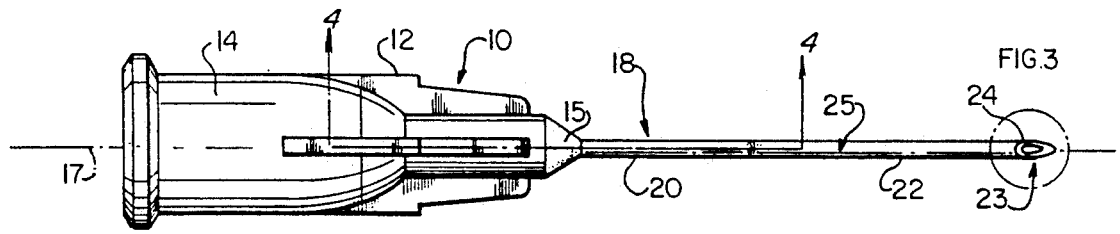
FIG. 2 is a rear elevation of the cannula of the present invention.
Figure 4:
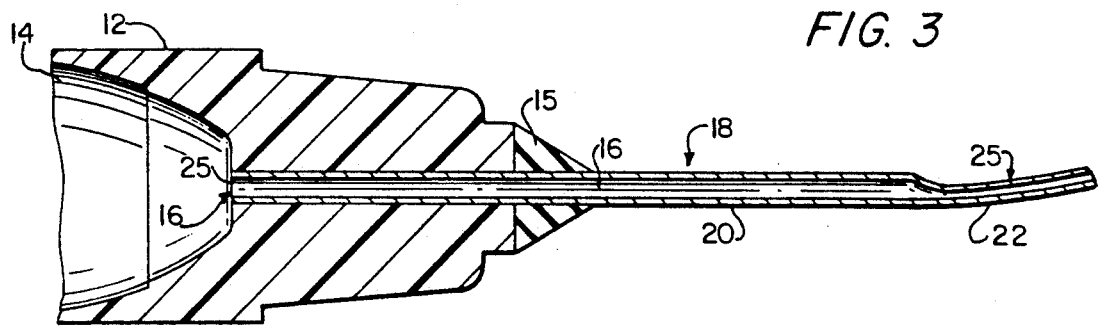
FIG. 4 is an enlarged sectional view taken along the lines 4—4 of FIG. 2.

A nuclear hydrolysis cannula generally denoted 10 is shown in FIGS. 1 and 2. In the preferred embodiment, the cannula 10 has a hub 12 which contains a female luer-lock fitting 14 for attachment to a syringe. The hub 12 has a tapered shield 15 on the end opposite the luer-lock fitting and has a passageway 16 therethrough which exists coaxially with a centrally located longitudinal axis 17 located in the horizontal plane (FIGS. 2 and 4). An example of a suitable hub is a standard 6% luer hub.

A needle generally denoted as 18 is securely located in the central passageway 16 and extends forwardly from hub 12 (FIG. 4). The needle 18 is fabricated from 25 gauge stainless steel hypodermic tubing and is composed of a first, or inner, linear section 20 which has an axis which extends forwardly from the hub 12 in a plane extending through and oriented in the central longitudinal axis 17 of the cannula. The first, or inner, linear section 20 is approximately 8.00 mm in length forwardly from its portion adjacent the base of shield 15. The needle 18 has a curved, or medial, second section 22 which is oriented in the horizontal plane in which axis 17 is located, however, the second section extends generally away from the longitudinal axis 17 of the cannula as best shown in FIG. 1. Further, the needle 18 has a distal end 23 with a truncated surface 24 provided on the outer end of second section 22. In the preferred embodiment, the length of the axial component L of the needle 18 from the base of shield 15 to the outer end of distal end 23 is 20.00 mm as shown in FIG. 1. Also, the distal end is radially spaced from axis 17 a distance R which is approximately 5.0 mm.

The second section 22 of the needle has a flattened surface 25 formed by rolling, pressing or any other suitable method (FIGS. 1,2,4). In the preferred embodiment, the flattened surface 25 of the needle extends inwardly from the truncated surface 24 and terminates inwardly at a point at more than 10.00 mm inwardly from surface 24 as measured along axis 17; however any desired length of the needle may be flattened. The flattened surface 25 of second section 22 of the needle 18 permits the surgeon to rotate the nucleus, achieve good cleavage planes and engage, penetrate, and irrigate additional tissue.

The curved second section 22 of the needle 18 bends away from the central longitudinal axis 17 of the cannula (FIG. 1). More specifically, the curved second section 22 has a curvature which defines with the first section 20 a concave aspect which is directed away from the central longitudinal axis 17. In the preferred embodiment, the curved zone of the needle extends between the truncated surface 24 and a point 8.00 mm outward from the base of the tapered shield 15. The radius of curvature for the second section 22 of the needle is 19.00 mm. The curved second section 22 of the needle provides the surgeon with improved maneuverability when compared to straight needles. Consequently any desired area of the anterior wall of the capsule can be engaged by the outer end of the needle.

Figure 3:
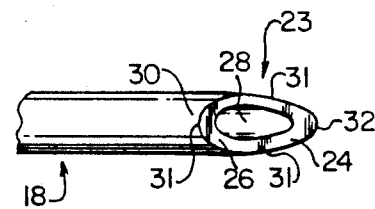
FIG. 3 is an enlarged view of the tip of the cannula.

The distal end 23 of the needle 18 includes a truncated surface 24 comprising a generally beveled surface 26 with an interior passageway 28 as shown in FIG. 3. The beveled surface 26 is oval in shape, i.e. rounded at both ends, to provide a rounded tip 32. The edge of the beveled surface 26, including the rounded tip 32, is sharpened to provide a cutting edge 31. The beveled surface 26 is toward the concave aspect of the needle 18 and away from the central longitudinal axis 17. The edge 31 will readily cut into tissue as the needle 18 is inserted into the lens of the eye thereby permitting movement of the needle to the rear portion of the lens prior to irrigation with a balanced salt solution.

The cutting edge 31 of the needle terminates at the rounded tip 32 as shown in FIG. 3. The rounded tip 32 permits the isolation and separation of the inner nucleus from the outer nucleus. The combination of the beveled, sharpened edge 31 and rounded tip 32 permit the isolation of several nuclei (multilamellar delineation) through deeper penetration into the inner nuclei and subsequent removal of the separated nucleus for additional irrigation.

Figure 5:
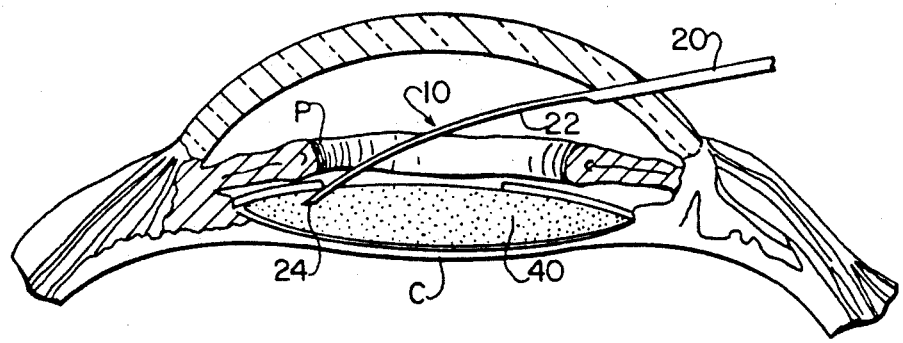
FIG. 5 is a sectional view of the eye illustrating the initial surgical procedures employed in use of the subject invention.
Figure 6:
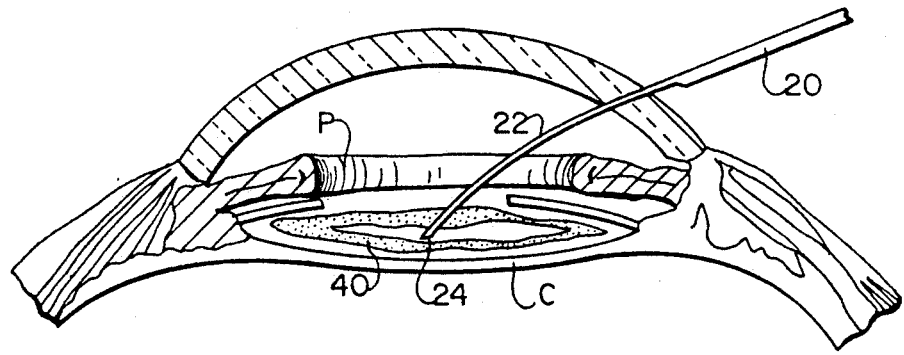
FIG. 6 is a sectional view subsequent to FIG. 5 in the surgical procedure.

In a typical cataract removal procedure, the pupil P is dilated as shown in FIG. 5 and cannula 10 is inserted through the anterior face of the capsule and moved inwardly of the lens 40 until the truncated surface 24 is adjacent the anterior portion of the capsule following which fluid under pressure is injected through the cannula to create a fluid wave which passes behind the entire nucleus of the lens to separate it from the cortex and the capsule C to complete a hydrodissection procedure. The cannula is next inserted into the body of the nucleus of the lens 40 as shown in FIG. 6 so that a hydrodelamination procedure can be performed. The aforementioned insertion of the cannula into the nucleus is performed with a minimum of difficulty due to the fact that the cannula has the sharp cutting edge 31 so that it can be maneuvered upwardly and downwardly and from side to side to provide an incision permitting the needle to move further into the nucleus. The creation of this incision makes it possible to isolate several of the cleavage planes of the lens. The injection of fluid into the nucleus effects completion of the hydrodelamination procedure which is then repeated several times, if necessary, to effect removal of the lens material from the capsule. The fact that the shaft of the cannula is provided with the flattened surface 25 permits the cannula to be used to maneuver the nucleus to accentuate the creation of cleavage planes and to free-up the nucleus so that further tissue may be engaged, penetrated and irrigated.

It will be understood that the spirit and scope of the invention is not limited to the preferred embodiment but is to be limited solely by the appended claims.

I claim:

1. A nuclear hydrolysis cannula for use in removing cataracts during the phases of hydrodissection and hydrodelamination/hydrodelineation/hydrodemarcation, comprising:

a hub portion having a proximal end, a distal end, and a centrally disposed longitudinal axis;

a one-piece needle having a straight first section a curved second section, a first end at said first section, and a second end at said second section, said first end being mounted in said distal end of said hub portion with said needle extending forwardly beyond said distal end, said first section being coaxial with said longitudinal axis of said hub, said second section extending away from said longitudinal axis and terminating at said second end without curving inwardly towards said longitudinal axis, and said second end being trucated to define a beveled surface and having a sharpened edge with a rounded tip.

2. The nuclear hydrolysis cannula of claim 1, wherein said second section has a flattened surface extending along its length.

3. The nuclear hydrolysis cannula of claim 1 wherein said hub at said proximal end is configured to mate with a standard syringe.

4. The nuclear hydrolysis cannula of claim 3, wherein said hub at said proximal end includes a female luer-look fitting.

5. The nuclear hydrolysis cannula of claim 1, wherein said first section extends outwardly from said distal end of said hub portion approximately 8.00 mm, and said needle from said distal end of said hub portion to said second end has an axial length of approximately 20.00 mm.

6. The nuclear hydrolysis cannula of claim 1, wherein said second section has a radius of curvature of approximately 19.00 mm.

7. The nuclear hydrolysis cannula of claim 6, wherein said second end is disposed a distance of approximately 5.00 mm from said longitudinal axis.

8. The nuclear hydrolysis cannula of claim 1, wherein said second section of said needle has a curvature which defines with said first section a concave aspect which is directed away from said longitudinal axis.

9. The nuclear hydrolysis cannula of claim 1, wherein said beveled surface is directed away from said longitudinal axis.

10. The nuclear hydrolysis cannula of claim 9, wherein said second section has a flattened surface extending along its length.

11. A nuclear hydrolysis cannula for use in removing cataracts during the phases of hydrodissection and hydrodelamination/hydrodelineation/hydrodemarcation, comprising:

a hub portion having a proximal end, a distal end, and a centrally disposed longitudinal axis;

a one-piece needle having a straight first section a curved second section, a first end at said first section, and a second end at said second section, said first end being mounted in said distal end of said hub portion with said needle extending forwardly beyond said distal end, said first section being coaxial with said longitudinal axis of said hub, said second section extending away from said longitudinal axis and terminating at said second end without curving inwardly towards said longitudinal axis, said second end being trucated to define a beveled surface and having a sharpened edge with a rounded tip, said first section extending outwardly from said distal end of said hub portion approximately 8.00 mm, said needle from said distal end of said hub portion to said second end having an axial length of approximately 20.00 mm, said second section having a radius of curvature of approximately 19.00 mm, and said second end being disposed a distance of approximately 5.00 mm from said longitudinal axis.

12. The nuclear hydrolysis cannula of claim 11, wherein said second section has flattened surface extending along its length.

13. The nuclear hydrolysis cannula of claim 11, wherein said hub at said proximal end is configured to mate with a standard syringe.

14. The nuclear hydrolysis cannula of claim 13, wherein said hub at said proximal end includes a female luer-lock fitting.

15. The nuclear hydrolysis cannula of claim 11, wherein said second section of said needle has a curvature which defines with said first section a concave aspect which is directed away from said longitudinal axis.

16. The nuclear hydrolysis cannula of claim 11, wherein said beveled surface is directed away from said longitudinal axis.

17. The nuclear hydrolysis cannula of claim 16, wherein said second section has a flattened surface extending along its length.

18. A nuclear hydrolysis cannula for use in removing cataracts during the phases of hydrodissection and hydrodelamination/hydrodelineation/hydrodemarcation, comprising:
  a hub portion having a proximal end, a distal end, and a centrally disposed longitudinal axis;
  a one-piece needle having a straight first section a curved second section, a first end at said first section, and a second end at said second section, said first end being mounted in said distal end of said hub portion with said needle extending forwardly beyond said distal end, said first section being coaxial with said longitudinal axis of said hub, said second section having a curvature which defines with said first section a concave aspect which is directed away from said longitudinal axis, and said second end being truncated to define a beveled surface and having a sharpened edge with a rounded tip.

19. The nuclear hydrolysis cannula of claim 18, wherein said second section has a flattened surface extending along its length.

20. The nuclear hydrolysis cannula of claim 18 wherein said hub at said proximal end is configured to mate with a standard syringe.

21. The nuclear hydrolysis cannula of claim 20, wherein said hub at said proximal end includes a female luer-lock fitting.

22. The nuclear hydrolysis cannula of claim 18, wherein said first section extends outwardly from said distal end of said hub portion approximately 8.00 mm, and said needle from said distal end of said hub portion to said second end has an axial length of approximately 20.00 mm.

23. The nuclear hydrolysis cannula of claim 18, wherein said second section has a radius of curvature of approximately 19.00 mm.

24. The nuclear hydrolysis cannula of claim 23, wherein said second end is disposed a distance of approximately 5.00 mm from said longitudinal axis.

25. The nuclear hydrolysis cannula of claim 18, wherein said beveled surface is directed away from said longitudinal axis.

26. The nuclear hydrolysis cannula of claim 25, wherein said second section has a flattened surface extending along its length.

* * * * *